US012003880B2

(12) United States Patent
Richardson et al.

(10) Patent No.: US 12,003,880 B2
(45) Date of Patent: *Jun. 4, 2024

(54) IMAGE ROTATION USING SOFTWARE FOR ENDOSCOPIC APPLICATIONS

(71) Applicant: DePuy Synthes Products, Inc., Raynham, MA (US)

(72) Inventors: John Richardson, Westlake Village, CA (US); Laurent Blanquart, Westlake Village, CA (US); Jeremiah D. Henley, Salt Lake City, UT (US); Donald M. Wichern, Ogden, UT (US)

(73) Assignee: DePuy Synthes Products, Inc., Raynham, MA (US)

( * ) Notice: Subject to any disclaimer, the term of this patent is extended or adjusted under 35 U.S.C. 154(b) by 202 days.

This patent is subject to a terminal disclaimer.

(21) Appl. No.: 16/509,297

(22) Filed: Jul. 11, 2019

(65) Prior Publication Data

US 2019/0356867 A1 Nov. 21, 2019

Related U.S. Application Data

(63) Continuation of application No. 14/214,412, filed on Mar. 14, 2014, now Pat. No. 10,362,240.

(Continued)

(51) Int. Cl.
*H04N 5/262* (2006.01)
*A61B 1/00* (2006.01)
(Continued)

(52) U.S. Cl.
CPC ....... *H04N 5/2628* (2013.01); *A61B 1/00006* (2013.01); *A61B 1/000095* (2022.02);
(Continued)

(58) Field of Classification Search
CPC .. H04N 5/2628; H04N 5/2251; H04N 5/2253; H04N 5/23258; H04N 2005/2255;
(Continued)

(56) References Cited

U.S. PATENT DOCUMENTS

| 4,433,675 A | 2/1984 | Konoshima |
| 5,187,572 A | 2/1993 | Nakamura et al. |

(Continued)

FOREIGN PATENT DOCUMENTS

| JP | 2005328970 A | 12/2005 |
| JP | 2011-019549 | 2/2011 |
| WO | 2005031433 A1 | 4/2005 |

OTHER PUBLICATIONS

Holler Kurt et al. "Endoscopic Orientation Correct," Sep. 20, 2019, International Conference on Computer Analysis of Images and Patters. CAIP 2017: Computer Analysis of Images and Patterns; [Lecture Notes in Computer Science; Lec. Notes Computer], Springer, Berlin, Heidelberg, pp. 459-466.

(Continued)

*Primary Examiner* — Ayman A Abaza
(74) *Attorney, Agent, or Firm* — TechLaw Ventures, PLLC; Terrence J. Edwards

(57) ABSTRACT

An endoscopic device and system for image correction of a rotating sensor includes a hand-piece, a lumen comprising a distal tip, and an image sensor disposed within the lumen for providing visualization of an area. The image sensor is located near the distal tip of the lumen. The lumen is rotatable about an axis of the endoscope and with respect to the hand-piece. The endoscopic device and system further includes an image signal processing pipeline that is configured to rotate images to maintain a constant image horizon for a user on a display.

35 Claims, 9 Drawing Sheets

Related U.S. Application Data

(60) Provisional application No. 61/792,119, filed on Mar. 15, 2013.

(51) Int. Cl.

| | |
|---|---|
| *A61B 1/05* | (2006.01) |
| *H04N 23/50* | (2023.01) |
| *H04N 23/54* | (2023.01) |
| *H04N 23/68* | (2023.01) |

(52) U.S. Cl.
CPC ............ *A61B 1/00045* (2013.01); *A61B 1/05* (2013.01); *H04N 23/50* (2023.01); *H04N 23/54* (2023.01); *H04N 23/6812* (2023.01); *H04N 23/555* (2023.01)

(58) Field of Classification Search
CPC ............ A61B 1/00006; A61B 1/00009; A61B 1/0045; A61B 1/05
USPC .......................................................... 348/68
See application file for complete search history.

(56) References Cited

U.S. PATENT DOCUMENTS

| | | | |
|---|---|---|---|
| 5,241,170 A | | 8/1993 | Field, Jr. et al. |
| 5,877,819 A | | 3/1999 | Branson |
| 6,073,043 A | * | 6/2000 | Schneider ................ A61B 5/06 |
| | | | 128/899 |
| 6,272,269 B1 | | 8/2001 | Naum |
| 6,296,635 B1 | * | 10/2001 | Smith ........................ B25J 3/04 |
| | | | 606/1 |
| 6,331,156 B1 | | 12/2001 | Haefele et al. |
| 6,387,043 B1 | | 5/2002 | Yoon |
| 6,419,626 B1 | | 7/2002 | Yoon |
| 6,471,637 B1 | | 10/2002 | Green et al. |
| 6,485,414 B1 | | 11/2002 | Neuberger |
| 6,690,466 B2 | | 2/2004 | Miller et al. |
| 6,692,431 B2 | | 2/2004 | Kazakevich |
| 6,899,675 B2 | | 5/2005 | Cline et al. |
| 6,916,286 B2 | | 7/2005 | Kazakevich |
| 6,921,920 B2 | | 7/2005 | Kazakevich |
| 6,961,461 B2 | | 11/2005 | MacKinnon et al. |
| 7,037,258 B2 | | 5/2006 | Chatenever et al. |
| 7,037,259 B2 | | 5/2006 | Hakamata et al. |
| 7,189,226 B2 | | 3/2007 | Auld et al. |
| 7,211,042 B2 | | 5/2007 | Chatenever et al. |
| 7,258,663 B2 | | 8/2007 | Doguchi et al. |
| 7,540,645 B2 | | 6/2009 | Kazakevich |
| 7,544,163 B2 | | 6/2009 | MacKinnon et al. |
| 7,783,133 B2 | | 8/2010 | Dunki-Jacobs et al. |
| 7,794,394 B2 | | 9/2010 | Frangioni |
| 7,833,152 B2 | | 11/2010 | Chatenever et al. |
| 10,362,240 B2 | | 7/2019 | Richardson et al. |
| 2001/0018553 A1 | | 8/2001 | Krattiger et al. |
| 2001/0030744 A1 | | 10/2001 | Chang |
| 2003/0142753 A1 | * | 7/2003 | Gunday ................... H04N 7/18 |
| | | | 375/240.29 |
| 2004/0249267 A1 | | 12/2004 | Gilboa |
| 2005/0159740 A1 | | 7/2005 | Paul et al. |
| 2005/0234302 A1 | | 10/2005 | MacKinnon et al. |
| 2005/0250983 A1 | | 11/2005 | Tremaglio et al. |
| 2006/0069314 A1 | | 3/2006 | Farr |
| 2008/0045800 A2 | | 2/2008 | Farr |
| 2008/0071142 A1 | * | 3/2008 | Gattani ................ A61B 1/0005 |
| | | | 600/117 |
| 2008/0159653 A1 | * | 7/2008 | Dunki-Jacobs .......... A61B 1/04 |
| | | | 382/293 |
| 2009/0012361 A1 | | 1/2009 | MacKinnon et al. |
| 2009/0220156 A1 | * | 9/2009 | Ito ...................... G06K 9/00248 |
| | | | 382/201 |
| 2009/0292168 A1 | | 11/2009 | Farr |
| 2010/0022829 A1 | | 1/2010 | Irion et al. |
| 2010/0033170 A1 | * | 2/2010 | Velasquez ............ G01D 5/3473 |
| | | | 324/207.25 |
| 2010/0048999 A1 | | 2/2010 | Boulais et al. |
| 2010/0125166 A1 | | 5/2010 | Henzler |
| 2010/0249817 A1 | | 9/2010 | Mark |
| 2010/0286475 A1 | * | 11/2010 | Robertson .......... A61B 1/00096 |
| | | | 600/104 |
| 2011/0181840 A1 | | 7/2011 | Cobb |
| 2011/0237882 A1 | | 9/2011 | Saito |
| 2011/0237884 A1 | | 9/2011 | Saito |
| 2011/0263941 A1 | | 10/2011 | Wright et al. |
| 2012/0004508 A1 | | 1/2012 | McDowall et al. |
| 2012/0041267 A1 | | 2/2012 | Benning et al. |
| 2012/0078052 A1 | | 3/2012 | Cheng |
| 2012/0257030 A1 | | 10/2012 | Lim et al. |
| 2012/0307030 A1 | | 12/2012 | Blanquart |
| 2013/0060086 A1 | | 3/2013 | Talbert et al. |
| 2013/0155305 A1 | | 6/2013 | Shintani |

OTHER PUBLICATIONS

Anonymous: "Olympus Microscopy Resource 4,7-12 Center: Geometrical Transformation—Java Tutorial," Dec. 31, 2012 (Dec. 31, 2012), XP055294458, Retrieved from the Internet: URL:http://www.olympusmicro.com/primer/java/digitalimaging/processing/geometricaltransformation/index.html [retrieved on Aug. 9, 2016].

Anonymous: "Potentiometergeber—Wikipedia," Oct. 8, 2012 (Oct. 8, 2012), XP055294467, Retrieved from the Internet: URL:https://de.wikipedia.org/w/index.php?title=Potentiometergeber&01did=109084688 [retrieved on Aug. 9, 2016].

Anonymous: "Resolver (electrical)—Wikipedia, the free encyclopedia," Mar. 2, 2013 (Mar. 2, 2013), XP055294466, Retrieved from the Internet: URL:https://en.wikipedia.org/w/index.php?title=Resolver (electrical)&oldid=541673781 [retrieved on-Aug. 9, 2016].

Anonymous: "Rotary encoder—Wikipedia, the free encyclopedia," Mar. 5, 2013 (Mar. 5, 2013), XP055294463, Retrieved from the Internet: URL:https://en.wikipedia.org/w/index.php?title=Rotary encoder&oldid=542165237 [retrieved on Aug. 9, 2016].

Eberly, David: "Integer-Based Rotations of 4, 7-12 Images Contents," Mar. 2, 2008 (Mar. 2, 2008), pp. 1-5, XP055294442, Retrieved from the Internet: URL:http://www.geometrictools.com/Documentation/IntegerBasedRotation.pdf [retrieved on Aug. 9, 2016].

Computer generated English translation of Japanese Publication No. 2011-019549, Published Feb. 3, 2011.

\* cited by examiner

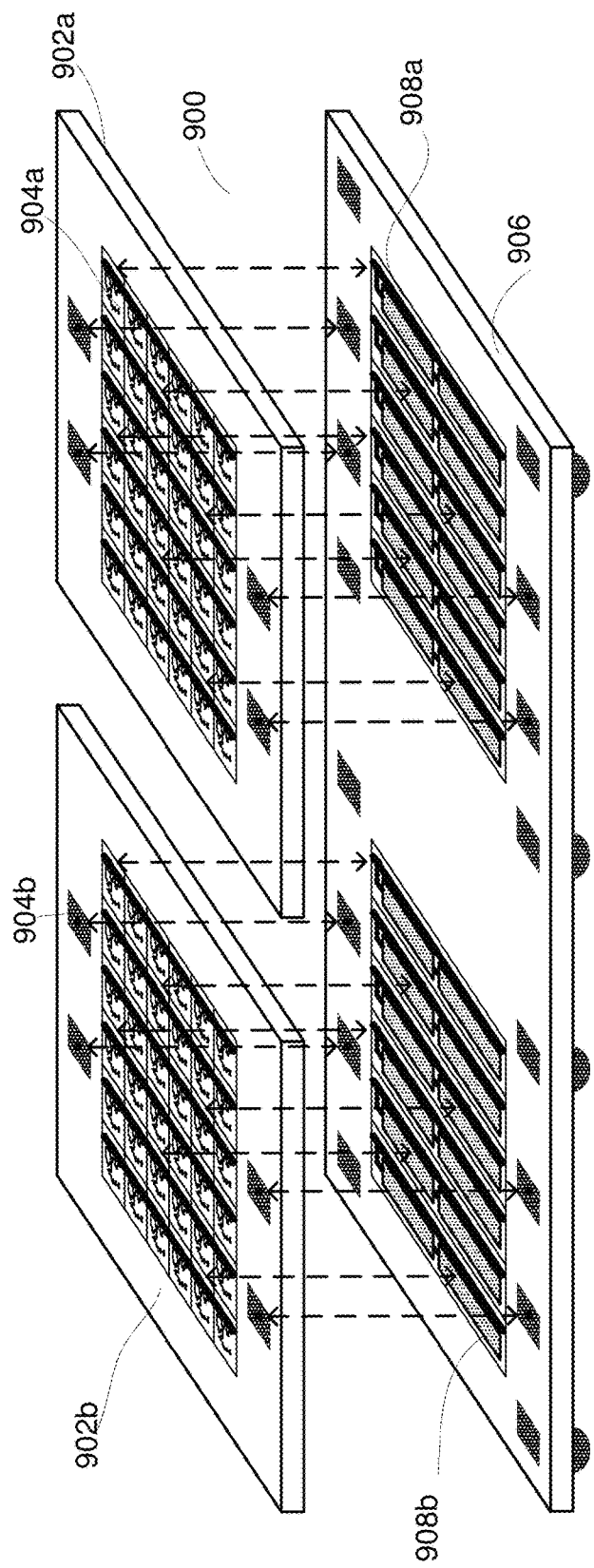
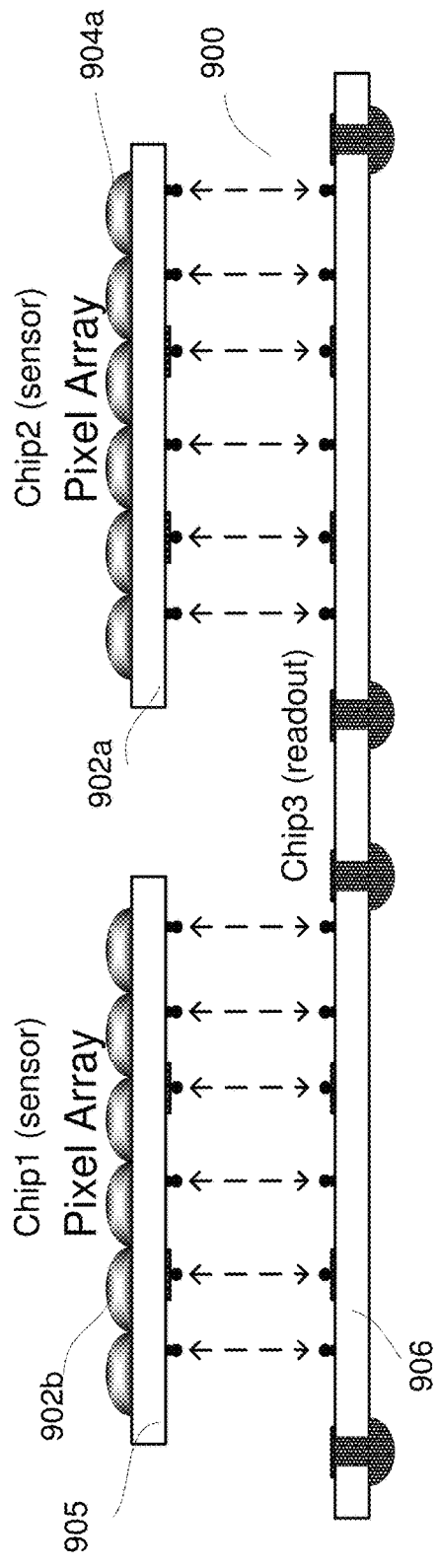
FIG. 9A
FIG. 9B

IMAGE ROTATION USING SOFTWARE FOR ENDOSCOPIC APPLICATIONS

CROSS-REFERENCE TO RELATED APPLICATIONS

This application is a continuation of U.S. application Ser. No. 14/214,412, filed Mar. 14, 2014 (U.S. Pat. No. 10,362, 240) and claims the benefit of U.S. Provisional Application No. 61/792,119, filed Mar. 15, 2013, which are incorporated herein by reference in their entirety, including but not limited to those portions that specifically appear hereinafter, the incorporation by reference being made with the following exception: In the event that any portion of the above-referenced applications are inconsistent with this application, this application supersedes said above-referenced applications.

STATEMENT REGARDING FEDERALLY SPONSORED RESEARCH OR DEVELOPMENT

Not Applicable.

BACKGROUND

Advances in technology have provided advances in imaging capabilities for medical use. One area that has enjoyed some of the most beneficial advances is that of endoscopic surgical procedures because of the advances in the components that make up an endoscope.

Conventional, digital video systems used for laparoscopy, arthroscopy, ENT, gynecology and urology are based upon conventional, rigid endoscopes, which are optically and mechanically coupled to a separate hand-piece unit. The hand-piece may comprise an image sensor(s). Image information is optically transmitted along the length of the endoscope, after which it is focused upon the sensor via an optical coupler. The endoscope is free to rotate with respect to the image sensor and the operator will typically exploit this fact to cover a greater range of a scene of a surgical site when using endoscopes with a non-zero viewing angle. The orientation of the image as seen on the viewing display or monitor depends on the orientation of the hand-piece unit with respect to the scene. Generally the user or operator of the hand-piece wishes the vertical direction in the image to be the same direction as their own upright direction.

BRIEF DESCRIPTION OF THE DRAWINGS

Non-limiting and non-exhaustive implementations of the disclosure are described with reference to the following figures, wherein like reference numerals refer to like parts throughout the various views unless otherwise specified. Advantages of the disclosure will become better understood with regard to the following description and accompanying drawings where:

FIGS. 9A and 9B illustrate a perspective view and a side view, respectively, of an implementation of an imaging sensor having a plurality of pixel arrays for producing a three dimensional image, wherein the plurality of pixel arrays and the image sensor are built on a plurality of substrates.

DETAILED DESCRIPTION

Figure 1:
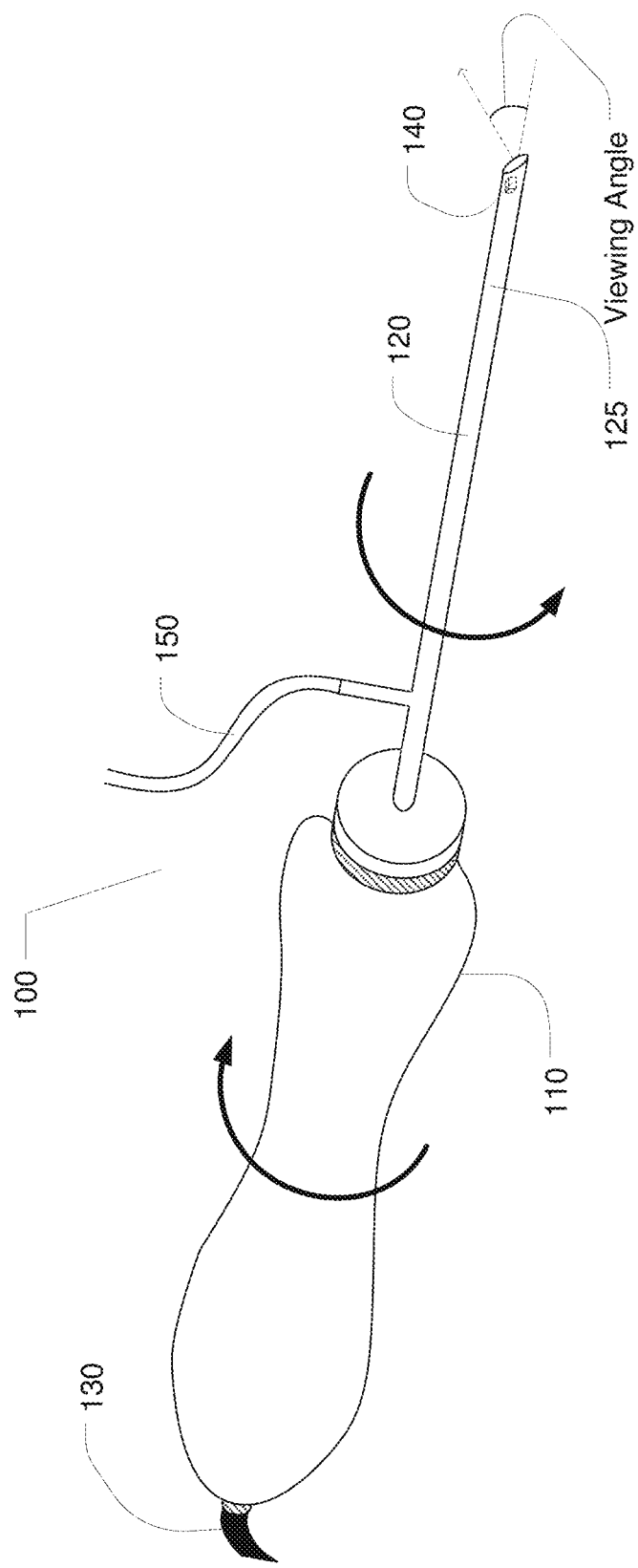
FIG. 1 illustrates an endoscopic device in accordance with the principles and teachings of the disclosure.

For reasons of cost and simplicity, an improved endoscope design concept involves placing an image sensor within the endoscope itself and transmitting the image data to the remainder of the camera system electrically. In an implementation of the disclosure, the image sensor may be placed within a distal end of the endoscope. The challenge for such a system is to maintain high image quality using a sensor that is space constrained. This challenge may be overcome by a system that incorporates a monochrome image sensor with minimal peripheral circuitry, connection pads and logic. Color information is provided by pulsing different frames with different wavelengths of light using, e.g., laser or LED light sources. The image sensor is able to capture frames within $1/120$ s or less, thereby producing full color video at a rate of 60 Hz or higher.

Another challenge arising from this approach is in providing a final image orientation for a user, which still reflects the hand-piece orientation with respect to the scene. One, purely mechanical approach is to have the sensor be rigidly coupled to the hand-piece and to rotate the endoscope, including the lens stack, at the front end independently. This may be accomplished by incorporating two concentric tubes. The system allows for a distal prism to rotate, which changes the angle of view of the user or operator, while the sensor remains fixed at a constant location. This allows the device to be used in the same manner as expected by a user or operator experienced in using conventional rigid endoscopy systems. The user or operator may rotate an outer lumen, thereby changing the angle of view, while the sensor remains in a fixed position and the image viewable on screen remains at a constant horizon. The prism may rotate while the sensor does not rotate, such that the user does not lose orientation.

This disclosure extends to an alternative approach in which the sensor is rigidly coupled, along with the lens stack, to a single tube while the digital images are rotated in the image signal processing pipeline or chain (ISP). The disclosure contemplates using a digital representation of the angle of the endoscope tube with respect to the hand-piece that is continuously available to the ISP during operation. Several approaches to this are possible, as described more fully herein.

The disclosure also extends to a solution for endoscopy applications in which the image sensor is resident at the distal end of the endoscope. With an image sensor located in the distal end of an endoscopic device, there are challenges present, which are not at issue when the imaging sensor is located remotely from the distal end of the endoscopic device. For example, when a user or operator rotates or changes the angle of the endoscopic device, which is common during a surgery, the image sensor will change orientation and the image horizon shown on screen will also change. What is needed are devices and systems that accommodate an image sensor being located in the distal end of the endoscopic device without changing the orientation and maintaining a constant image horizon for the user or operator. As will be seen, the disclosure provides devices and systems that can do this in an efficient and elegant manner.

In the following description of the disclosure, reference is made to the accompanying drawings, which form a part hereof, and in which is shown by way of illustration specific implementations in which the disclosure may be practiced. It is understood that other implementations may be utilized and structural changes may be made without departing from the scope of the disclosure.

It must be noted that, as used in this specification and the appended claims, the singular forms "a," "an," and "the" include plural referents unless the context clearly dictates otherwise.

As used herein, the terms "comprising," "including," "containing," "characterized by," and grammatical equivalents thereof are inclusive or open-ended terms that do not exclude additional, unrecited elements or method steps.

Further, where appropriate, functions described herein can be performed in one or more of: hardware, software, firmware, digital components, or analog components. For example, one or more application specific integrated circuits (ASICs) can be programmed to carry out one or more of the systems and procedures described herein. Certain terms are used throughout the following description and Claims to refer to particular system components. As one skilled in the art will appreciate, components may be referred to by different names. This document does not intend to distinguish between components that differ in name, but not function.

Referring now to FIG. 1, an endoscopic device of the disclosure is illustrated. The mechanical structure of the endoscope 100 of the disclosure comprises a hand-piece unit 110 and an endoscope tube 120, which freely rotate relative to each other. As illustrated best in FIG. 1, the endoscope may also comprise an electrical cable 130 attached to the hand-piece 110. A light cable 150 may be attached to the endoscope 120. An image sensor 140 may be located within the hand-piece 110 or the endoscope tube 120, such that the rotation of the hand-piece 110 relative to the endoscope tube 120 creates an image horizon that may change depending upon the user's orientation of the hand-piece 110. In an implementation, the image sensor 140 may be located in the distal end of the endoscope tube 120, such that the rotation of the hand-piece 110 relative to the endoscope tube 120 creates an image horizon that may change depending upon the user's orientation of the hand-piece 110. To compensate for this changing orientation, the disclosure may utilize the following devices, methods and systems to detect an angle of the hand-piece 110 with respect to the endoscope tube 120.

Figure 2:
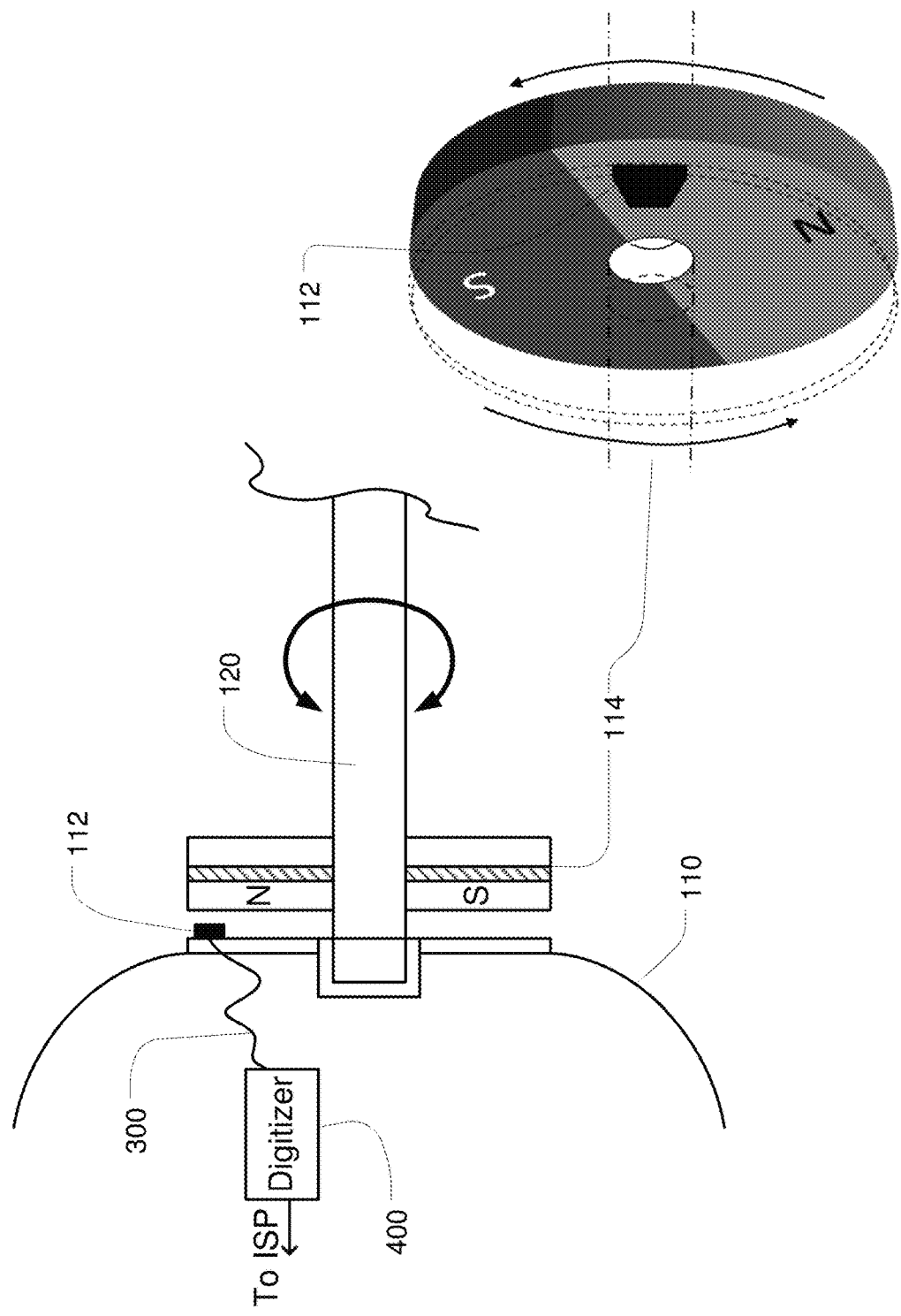
FIG. 2 illustrates an embodiment of an angle sensor in accordance with the principles and teachings of the disclosure.

Referring now to FIG. 2, in one implementation, a rotation-detecting Hall-effect sensor 112 may be located in the hand-piece 110. The sensor 112 may be used to detect the angle of a diametrically-polarized, magnetic annulus or disk 114 illustrated in FIG. 2. This type of Hall-effect sensor 112 produces a voltage, which indicates the direction of the magnetic field and may be used to determine the angle of the annulus or disk 114 and thus, the angle of the endoscope tube 120.

Figure 3:
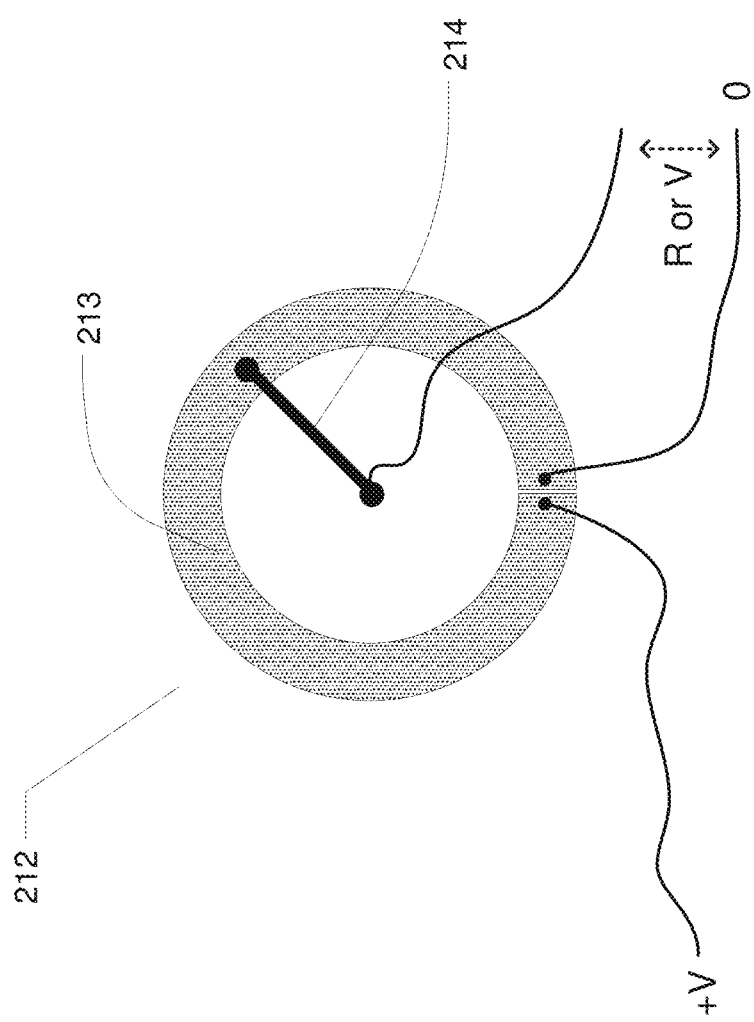
FIG. 3 illustrates an embodiment of an angle sensor in accordance with the principles and teachings of the disclosure.

Referring now to FIG. 3, in one implementation, a potentiometer 212 may be integrated into the junction between the hand-piece 110 and endoscope tube 120 illustrated in FIG. 1. The potentiometer 212 illustrated in FIG. 3 may comprise a carbon track or filament 213 that may be rigidly attached to the endoscope tube 120. The potentiometer 212 may further comprise a wiper 214 that may be rigidly attached to the hand-piece 110. It will be appreciated that the resistance may be measured between one end of the potentiometer 212 and the wiper 214, which will then indicate the angle for the configuration illustrated in FIG. 3. A potential divider arrangement may also be used for which the voltage seen at the wiper 214 will provide the angle measurement.

Figure 4:
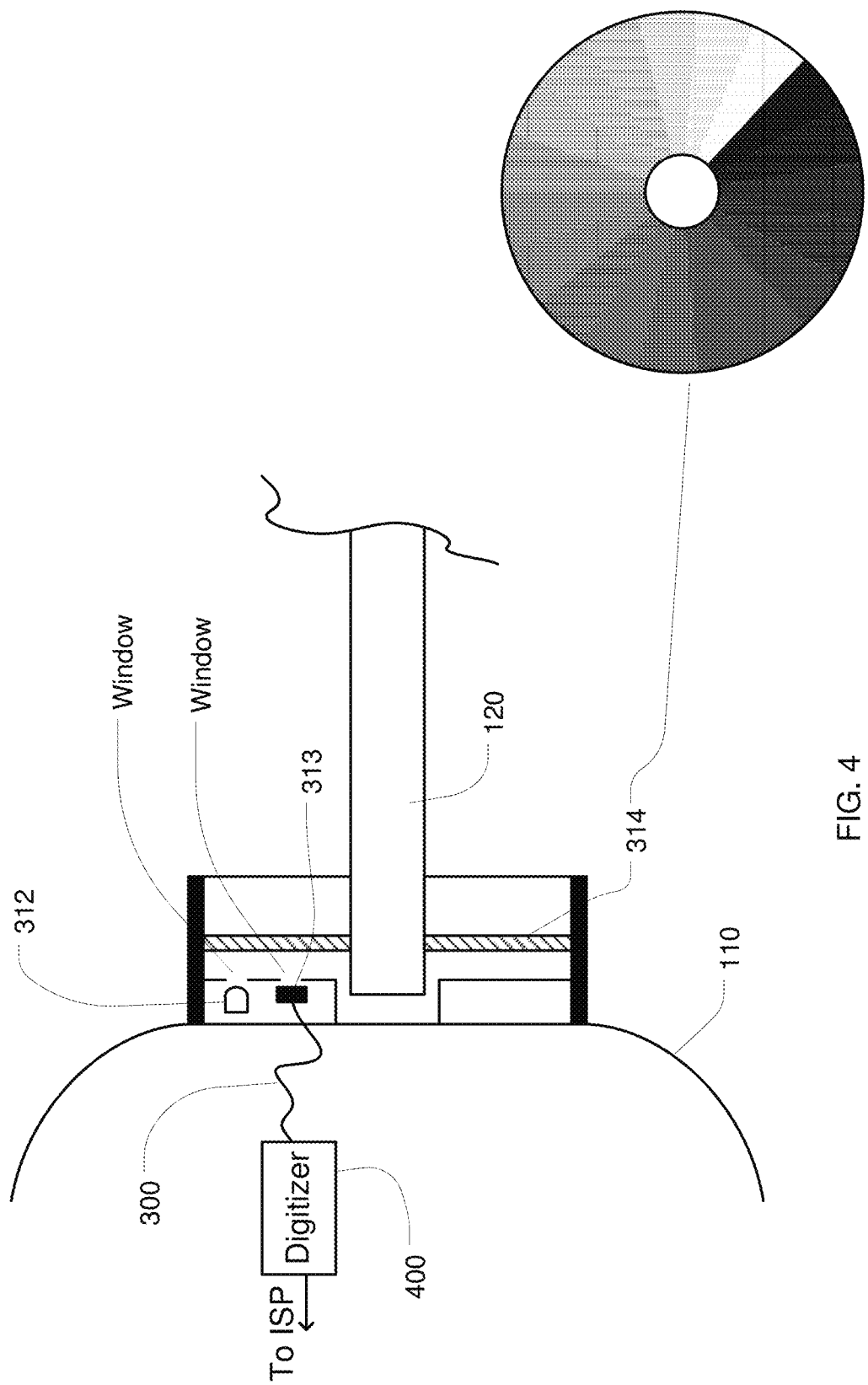
FIG. 4 illustrates an embodiment of an angle sensor in accordance with the principles and teachings of the disclosure.

Referring now to FIG. 4, in one implementation, a combination of an LED or similar light source 312 and a light detector 313, such as a photodiode or a phototransistor, may be incorporated into, or may be part of, or may be attached to the hand-piece 110. A continuous reflecting annulus or disk 314, with variable reflectivity, may be rigidly attached to the scope 120. The reflectivity may vary linearly with the angle, or a set of mirrors of suitably varying reflectivity, may be located at regular angular intervals. The amount of light from the light source 312, such as an LED source or other light source, reflected back at or to the light detector 313 indicates the angle.

For each of the implementations discussed above, any pertinent resultant voltage 300 is fed to an analog-digital converter (ADC) or digitizer 400. The digital number is then relayed to the ISP or the camera processing chain. The angle-sensing elements (112, 114; 212, 213, 214; and 312, 313, 314) discussed above may be placed into or as part of a fixed hand-piece 110 where the scope 120 rotates with respect to the fixed hand-piece system, which is illustrated best in FIGS. 5 and 6. In FIG. 6, the hand-piece 110 has been removed for purposes of clarity only.

Figure 5:
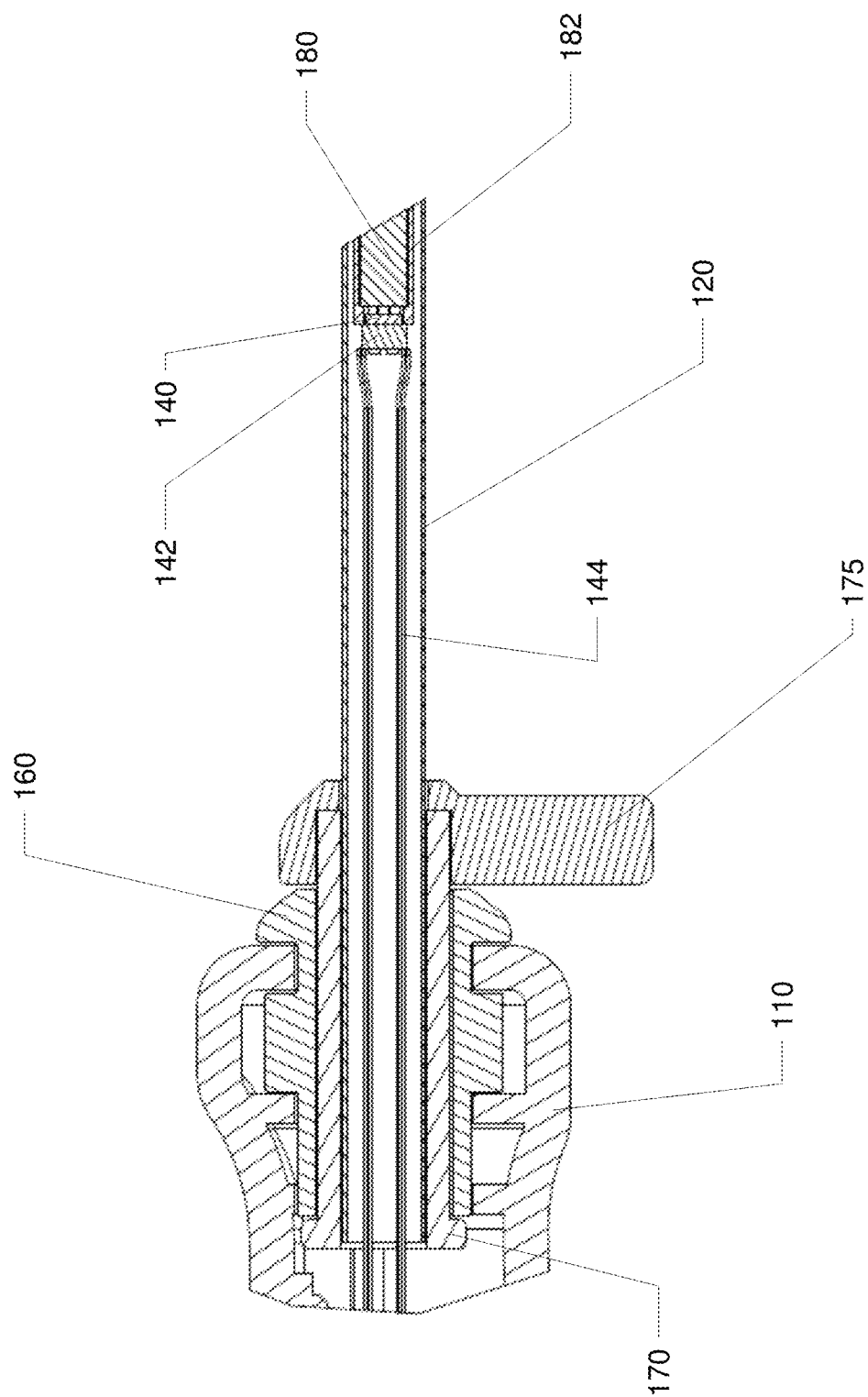
FIG. 5 illustrates one implementation of the endoscopic device, showing the ability of the outer lumen, along with a distal lens, prism, and sensor, of the endoscope to rotate to create a wide angle field of vision.
Figure 6:
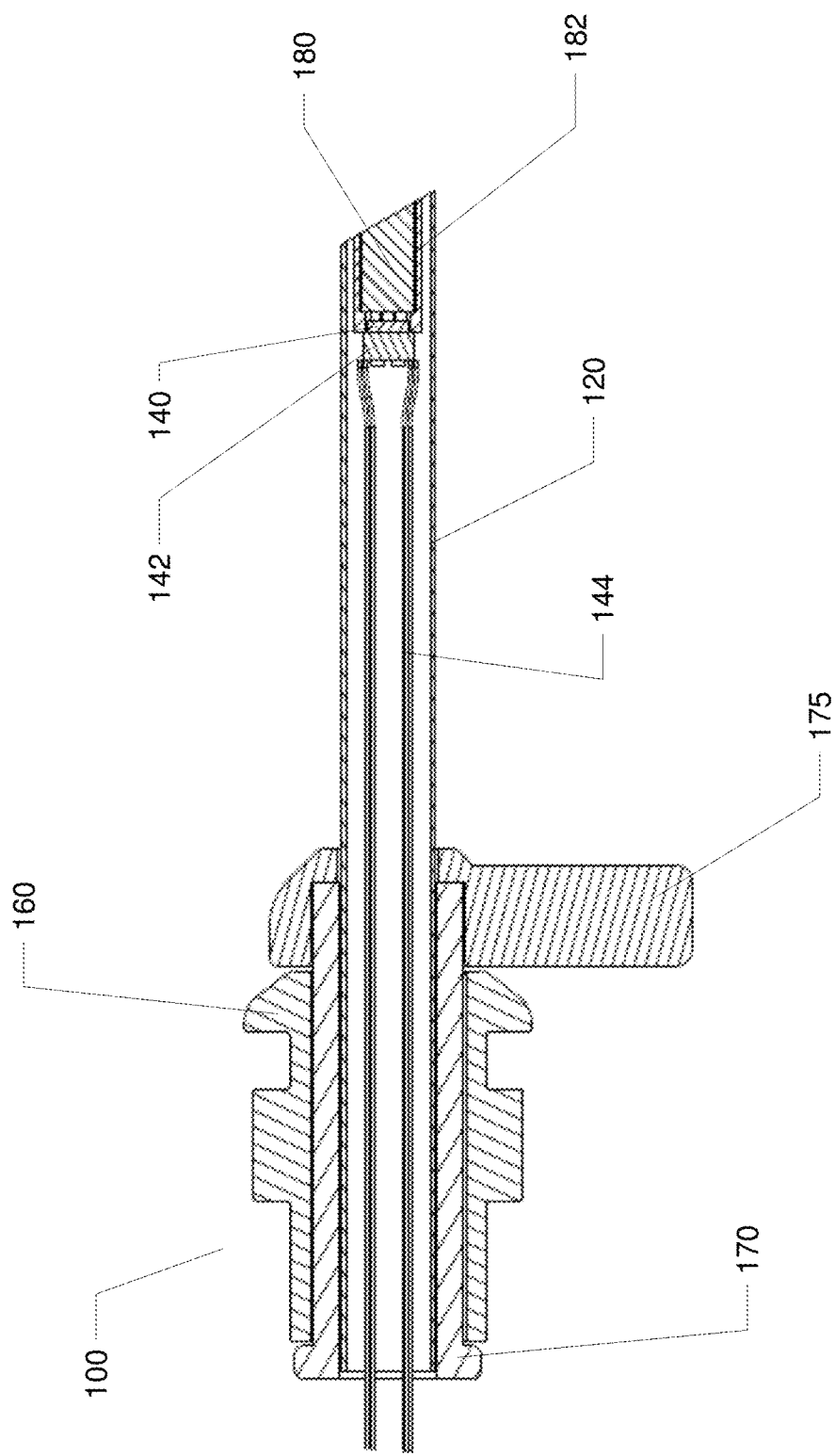
FIG. 6 illustrates one implementation of the endoscopic device, showing the ability of the outer lumen, along with a distal lens, prism, and sensor of the endoscope to rotate to create a wide angle field of vision.

As illustrated in FIGS. 5 and 6, the system may comprise a fixed hand-piece component 110 or set of components with a cylindrical opening on the distal end of the hand-piece. Within the cylindrical opening the scope 120 is restrained in the axial direction, but allowed to rotate about the axis. In addition to the components mentioned with respect to FIG. 1, the system may further comprise an interface component 160 that may be fixed to the hand-piece 110, a rotation sleeve 170, a rotation post 175, supporting electronics and circuitry 142 for the image sensor 140, a sensor wire harness 144, a lens stack 180, which includes a distal prism, located distally of the scope tube 120, and a lens holder 182. A method is shown in FIG. 6 where the combination of the rotation sleeve 170 and rotation post 175 act to constrain the scope 120 axially. There may be additional material between the interface component 160 and the rotation sleeve 170 to either add or reduce friction to achieve a torque that is low enough to be ergonomically pleasing, but high enough to prevent accidental rotation.

The rotation post 175 allows the user to rotate the scope 120 in a way that is similar to rotating a conventional scope (as shown in FIG. 1). As the rotation post 175 rotates, the entire scope assembly also rotates, including the distal imaging sensor 140 and attached lens stack 180. As can be seen, the viewing angle dictated by the distal prism changes and allows the user a broader or different view of the surgical scene.

For each embodiment, the rotating and fixed components of the angle detection system can be mounted to the rotation sleeve 170 and hand-piece 110, respectively.

It will be appreciated that the digital angle information may be made available to the image processing chain where it is sampled periodically (e.g., each frame) and quantized appropriately to, e.g., 5° or 10°, units. In order to prevent rapid angular oscillation of the final image between adjacent angles, a degree of hysteresis is required. One approach is to only allow an image transformation if the same quantized angle has been observed consistently within the previous n samples, where n would be tuned to the satisfaction of the user.

The basis of rotation of an image plane through angle θ is described by the following transformation:

$$x_2=(X_1-x_0)\cos\theta-(Y_1-y_0)\sin\theta+x_0$$

$$y_2=(Y_1-y_0)\cos\theta+(X_1-x_0)\sin\theta+y_0$$

where $(X_1, Y_1)$ are the original integer pixel coordinates, $(x_2,y_2)$ are the final real-number pixel coordinates and $(x_0,y_0)$ marks the axis of rotation. In general, unless θ is a multiple of 90°, $x_2$ and $y_2$ are not integers. The pixel locations in the final image buffer can be filled by truncating or rounding the $(x_2,y_2)$ values to integer coordinates $(X_2, Y_2)$:

$$X_2=\text{int}(x_2)$$

$$Y_2=\text{int}(y_2)$$

This approach results in multiple candidate cases and void pixels, however. The void pixels can be filled by nearest neighbor substitution, which has a resolution and artifact penalty, or by interpolation (e.g., bilinear or bicubic), requiring an occupancy investigation in their localities.

A more practical approach is afforded by taking each final integer pixel location and applying the inverse rotation transformation to arrive at real-number coordinates within the original plane:

$$x_1=(X_2-x_0)\cos\theta+(Y_2-y_0)\sin\theta+x_0$$

$$y_1=(Y_2-y_0)\cos\theta-(X_2-x_0)\sin\theta+y_0$$

Since pixel data within that plane are known to be at all integer coordinates, it is straightforward to derive an interpolated image content estimate. This interpolation can again either be bilinear or bicubic, e.g., Bilinear interpolation requires knowing only the closest four pixels, (two in each dimension). They are identified as $(X_a, Y_a)$, $(X_a, Y_b)$, $(X_b, Y_a)$ and $(X_b, Y_b)$, where:

$$X_a=\text{int}(x_1); X_b=1+\text{int}(x_1)$$

$$Y_a=\text{int}(y_1); Y_b=1+\text{int}(y_1)$$

The convolution kernel is described by:

$$\begin{pmatrix} (1-\alpha)(1-\beta) & \beta(1-\alpha) \\ \alpha(1-\beta) & \alpha\beta \end{pmatrix}$$

where;

$$\alpha=x_1-X_a$$

$$\beta=y_1-Y_a$$

in pixel units.

Figure 7A:
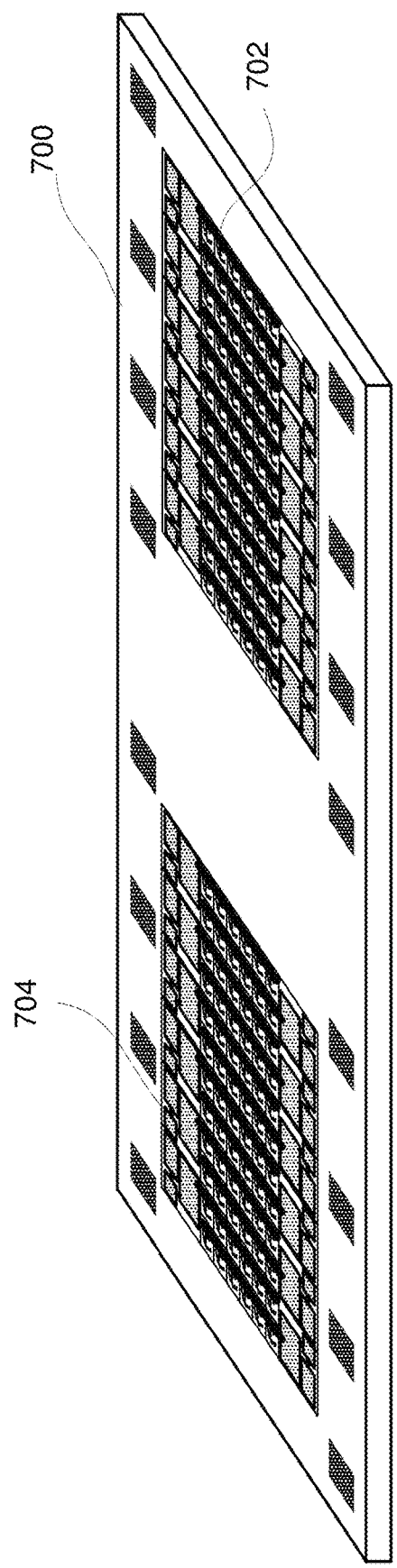
FIGS. 7A and 7B illustrate a perspective view and a side view, respectively, of an implementation of a monolithic sensor having a plurality of pixel arrays for producing a three dimensional image in accordance with the teachings and principles of the disclosure.
Figure 7B:
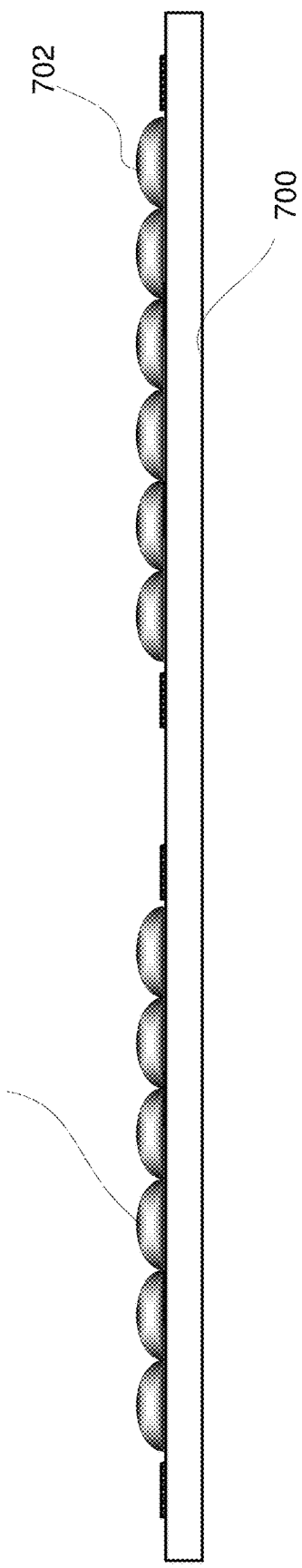

Referring now to FIGS. 7A and 7B, the figures illustrate a perspective view and a side view, respectively, of an implementation of a monolithic sensor 700 having a plurality of pixel arrays for producing a three dimensional image in accordance with the teachings and principles of the disclosure. Such an implementation may be desirable for three dimensional image capture, wherein the two pixel arrays 702 and 704 may be offset during use. In another implementation, a first pixel array 702 and a second pixel array 704 may be dedicated to receiving a predetermined range of wave lengths of electromagnetic radiation, wherein the first pixel array 702 is dedicated to a different range of wave length electromagnetic radiation than the second pixel array 704.

Figure 8A:
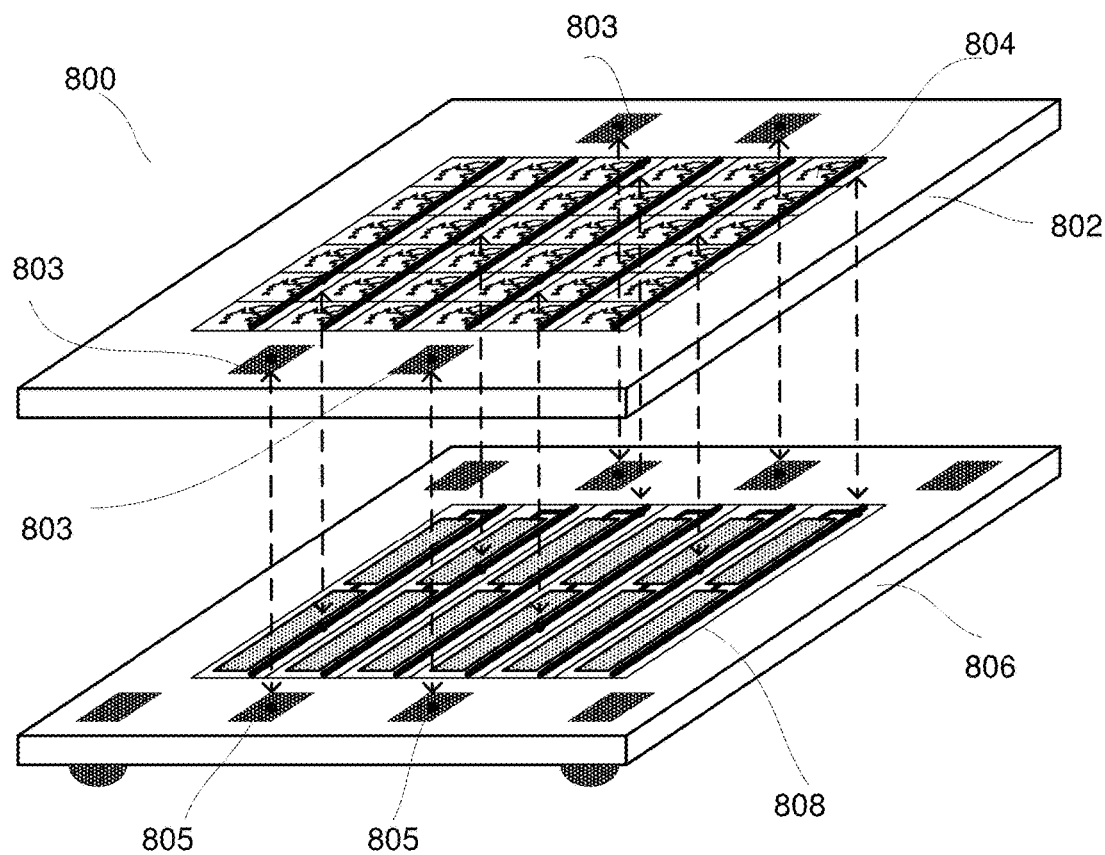
FIGS. 8A and 8B illustrate a perspective view and a side view, respectively, of an implementation of an imaging sensor built on a plurality of substrates, wherein a plurality of pixel columns forming the pixel array are located on the first substrate and a plurality of circuit columns are located on a second substrate and showing an electrical connection and communication between one column of pixels to its associated or corresponding column of circuitry.
Figure 8B:
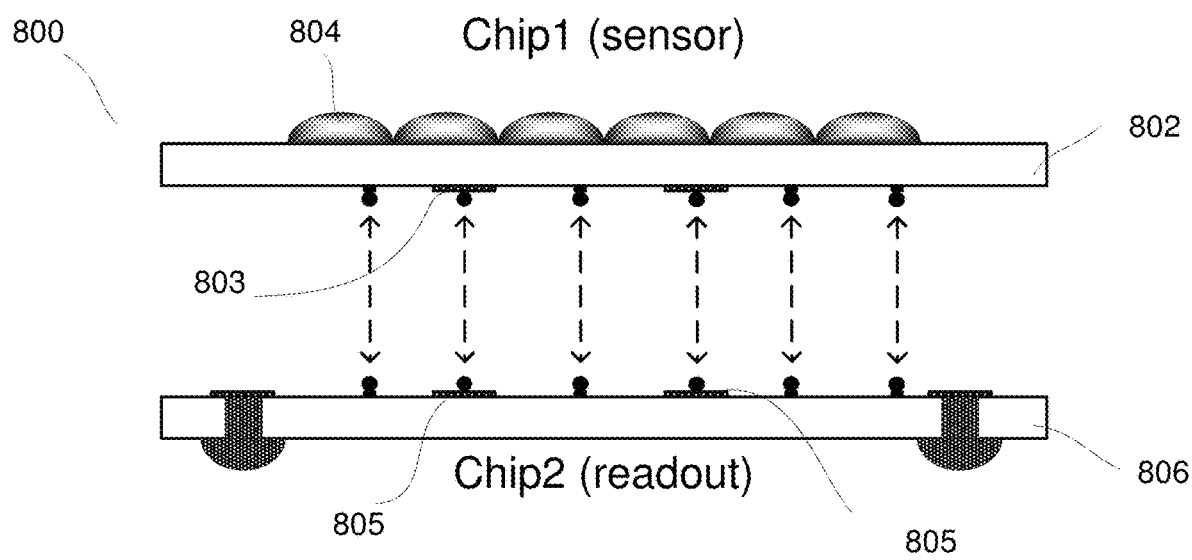

FIGS. 8A and 8B illustrate a perspective view and a side view, respectively, of an implementation of an imaging sensor 800 built on a plurality of substrates. As illustrated, a plurality of pixel columns 804 forming the pixel array are located on the first substrate 802 and a plurality of circuit columns 808 are located on a second substrate 806. Also illustrated in the figure are the electrical connection and communication between one column of pixels to its associated or corresponding column of circuitry. In one implementation, an image sensor, which might otherwise be manufactured with its pixel array and supporting circuitry on a single, monolithic substrate/chip, may have the pixel array separated from all or a majority of the supporting circuitry. The disclosure may use at least two substrates/chips, which will be stacked together using three-dimensional stacking technology. The first 802 of the two substrates/chips may be processed using an image CMOS process. The first substrate/chip 802 may be comprised either of a pixel array exclusively or a pixel array surrounded by limited circuitry. The second or subsequent substrate/chip 806 may be processed using any process, and does not have to be from an image CMOS process. The second substrate/chip 806 may be, but is not limited to, a highly dense digital process in order to integrate a variety and number of functions in a very limited space or area on the substrate/chip, or a mixed-mode or analog process in order to integrate for example precise analog functions, or a RF process in order to implement wireless capability, or MEMS (Micro-Electro-Mechanical Systems) in order to integrate MEMS devices. The image CMOS substrate/chip 802 may be stacked with the second or subsequent substrate/chip 806 using any three-dimensional technique. The second substrate/chip 806 may support most, or a majority, of the circuitry that would have otherwise been implemented in the first image CMOS chip 802 (if implemented on a monolithic substrate/chip) as peripheral circuits and therefore have increased the overall system area while keeping the pixel array size constant and optimized to the fullest extent possible. The electrical connection between the two substrates/chips may be done through interconnects 803 and 805, which may be wirebonds, bump and/or TSV (Through Silicon Via).

FIGS. 9A and 9B illustrate a perspective view and a side view, respectively, of an implementation of an imaging sensor 900 having a plurality of pixel arrays for producing a three dimensional image. The three dimensional image sensor may be built on a plurality of substrates and may comprise the plurality of pixel arrays and other associated circuitry, wherein a plurality of pixel columns 904*a* forming the first pixel array and a plurality of pixel columns 904*b* forming a second pixel array are located on respective substrates 902*a* and 902*b*, respectively, and a plurality of circuit columns 908*a* and 908*b* are located on a separate substrate 906. Also illustrated are the electrical connections and communications between columns of pixels to associated or corresponding column of circuitry.

It will be appreciated that the teachings and principles of the disclosure may be used in a reusable device platform, a limited use device platform, a re-posable use device platform, or a single-use/disposable device platform without departing from the scope of the disclosure. It will be appreciated that in a re-usable device platform an end-user is responsible for cleaning and sterilization of the device. In a limited use device platform the device can be used for some specified amount of times before becoming inoperable. Typical new device is delivered sterile with additional uses requiring the end-user to clean and sterilize before additional uses. In a re-posable use device platform a third-party may reprocess the device (e.g., cleans, packages and sterilizes) a single-use device for additional uses at a lower cost than a new unit. In a single-use/disposable device platform a device is provided sterile to the operating room and used only once before being disposed of.

Additionally, the teachings and principles of the disclosure may include any and all wavelengths of electromagnetic energy, including the visible and non-visible spectrums, such as infrared (IR), ultraviolet (UV), and X-ray.

The foregoing description has been presented for the purposes of illustration and description. It is not intended to be exhaustive or to limit the disclosure to the precise form disclosed. Many modifications and variations are possible in light of the above teaching. Further, it should be noted that any or all of the aforementioned alternate implementations may be used in any combination desired to form additional hybrid implementations of the disclosure.

Further, although specific implementations of the disclosure have been described and illustrated, the disclosure is not to be limited to the specific forms or arrangements of parts so described and illustrated. The scope of the disclosure is to be defined by the claims appended hereto, any future claims submitted here and in different applications, and their equivalents.

What is claimed is:

1. An endoscopic device comprising:
a hand-piece;
an endoscope tube comprising a proximal end and a distal end, wherein the proximal end of the endoscope tube is rotatably connected to the hand-piece such that the proximal end and the distal end of the endoscope tube are rotatable about an axis of the endoscope tube and with respect to the hand-piece;
an image sensor disposed within the endoscope tube for providing visualization of an area, wherein the image sensor is located near the distal end of the endoscope tube;
a sensor for detecting rotation of the proximal end of endoscope tube relative to the hand piece; and
an image signal processing pipeline that is configured to rotate images counter to a direction of rotation of the proximal end of the endoscope tube relative to the hand piece to maintain a constant image horizon for a user on a display.

2. The endoscopic device of claim 1, wherein the sensor comprises an angle sensor for detecting an angle of rotation of the hand-piece relative to the proximal end of the endoscope tube, wherein the angle sensor is a rotation-detecting Hall-effect sensor.

3. The endoscopic device of claim 2, wherein the rotation-detecting Hall-effect sensor is located in the hand-piece.

4. The endoscopic device of claim 2, wherein the device further comprises a diametrically-polarized magnetic annulus and wherein the rotation-detecting Hall-effect sensor produces a voltage that is used to detect an angle of the diametrically-polarized, magnetic annulus.

5. The endoscopic device of claim 1, wherein the sensor comprises an angle sensor for detecting an angle of rotation of the hand-piece relative to the proximal end of the endoscope tube, wherein the angle sensor produces a voltage that is used to detect the angle of rotation of the hand-piece relative to the proximal end of the endoscope tube.

6. The endoscopic device of claim 1, wherein the sensor comprises an angle sensor for detecting an angle of rotation of the hand-piece relative to the proximal end of the endoscope tube, wherein the angle sensor is a potentiometer.

7. The endoscopic device of claim 6, wherein the potentiometer comprises a carbon filament, wherein the carbon filament of the potentiometer is disposed on said proximal end of the endoscope tube.

8. The endoscopic device of claim 1, wherein the sensor comprises an angle sensor for detecting an angle of rotation of the hand-piece relative to the proximal end of the endoscope tube, wherein the angle sensor comprises a light source and a photo diode that rotate relative to a gradient disc.

9. The endoscopic device of claim 8, wherein said photo diode detects the electromagnetic energy from said light source that is reflected by said gradient disc.

10. The endoscopic device of claim 1, wherein said image sensor incorporates a two-dimensional array of pixels capable of detecting electromagnetic radiation.

11. The endoscopic device of claim 1, wherein the image signal processing pipeline performs image rotation transformations upon images captured by the image sensor; and
wherein said image rotation transformation comprises taking each initial pixel's integer x,y coordinates and transforming them to final, real number pixel coordinates by applying a rotation kernel.

12. The endoscopic device of claim 11, wherein said image rotation transformation further comprises truncating the final, real number pixel coordinates to integer values, then assigning values to blank pixels in a final image using the values of nearby, filled pixels.

13. The endoscopic device of claim 12, wherein said assignment is performed using bilinear interpolation.

14. The endoscopic device of claim 12, wherein said assignment is performed using bicubic interpolation.

15. The endoscopic device of claim 13, wherein said assignment is performed using nearest neighbor substitution.

16. The endoscopic device of claim 1, wherein the image signal processing pipeline performs image rotation transformations upon images captured by the image sensor; and
wherein said image rotation transformation comprises taking each final pixel's integer x,y coordinates and transforming them to initial real number x,y coordinates by applying an inverse rotation kernel.

17. The endoscopic device of claim 16, wherein said image rotation transformation further comprises estimating a pixel value at the initial real number x,y coordinates, using data from one or more closest integer coordinate locations.

18. The endoscopic device of claim 17, wherein said estimation is performed using nearest neighbor substitution.

19. The endoscopic device of claim 17, wherein said estimation is performed using bilinear interpolation.

20. The endoscopic device of claim 17, wherein said estimation is performed using bicubic interpolation.

21. An endoscopic system comprising:
an endoscope unit comprising:
a hand-piece;
an endoscope tube comprising a proximal end and a distal end, wherein the proximal end of the endoscope tube is rotatably connected to the hand-piece such that the proximal end and the distal end of the endoscope tube are rotatable about an axis of the endoscope tube and with respect to the hand-piece;
an image sensor disposed within the endoscope tube for providing visualization of an area, wherein the image sensor is located near the distal end of the endoscope tube and the image sensor incorporates a two dimensional array of pixels capable of detecting electromagnetic radiation;
a sensor for detecting rotation of the proximal end of the endoscope tube relative to the hand piece; and
an image signal processing pipeline performs rotation transformations upon images captured by the image sensor, wherein the image signal processing pipeline is configured to rotate the images counter to a direction of rotation of the proximal end of the endoscope tube relative to the hand piece to maintain a constant image horizon for a user on a display.

22. A method of rotating an image in an endoscopic application comprising:
providing an endoscope unit comprising:
a hand-piece;
an endoscope tube comprising a proximal end and a distal end, wherein the proximal end of the endoscope tube is rotatably connected to the hand-piece such that the proximal end and the distal end of the endoscope tube are rotatable about an axis of the endoscope tube and with respect to the hand-piece;
an image sensor disposed within the endoscope tube for providing visualization of an area, wherein the image sensor is located near the distal end of the endoscope tube and incorporates a two dimensional array of pixels capable of detecting electromagnetic radiation; and
a sensor for detecting rotation of the proximal end of endoscope tube relative to the hand piece;
detecting an angle of rotation of the hand-piece relative to the proximal end of the endoscope tube using the sensor; and
performing image rotation transformations upon images captured by the image sensor using an image signal processing pipeline that is configured to rotate the images counter to a direction of rotation of the proximal end of the endoscope tube relative to the hand piece to maintain a constant image horizon for a user on a display.

23. The method of claim 22, wherein the step of performing image rotation transformation comprises taking each initial pixel's integer x,y coordinates and transforming them to final, real number pixel coordinates by applying a rotation kernel.

24. The method of claim 23, wherein said image rotation transformation further comprises truncating the final, real number pixel coordinates to integer values, then assigning values to blank pixels in a final image using the values of nearby, filled pixels.

25. The method of claim 24, wherein said assignment is performed using bilinear interpolation.

26. The method of claim 24, wherein said assignment is performed using bicubic interpolation.

27. The method of claim 24, wherein said assignment is performed using nearest neighbor substitution.

28. The method of claim 22, wherein the step of performing image rotation transformation comprises taking each final pixel's integer x,y coordinates and transforming them to initial real number x,y coordinates by applying an inverse rotation kernel.

29. The method of claim 28, wherein said image rotation transformation further comprises estimating a pixel value at the initial real number x,y coordinates, using the data from one or more closest integer coordinate locations.

30. The method of claim 28, wherein said estimation is performed using nearest neighbor substitution.

31. The method of claim 28, wherein said estimation is performed using bilinear interpolation.

32. The method of claim 28, wherein said estimation is performed using bicubic interpolation.

33. The endoscopic device of claim 1, wherein the sensor for detecting rotation of the proximal end of endoscope tube relative to the hand piece comprises a first portion and a second portion, wherein the first portion senses angular position of the second portion as the second portion rotates relative to the first portion;
wherein the first portion is fixed to one of the proximal end of the endoscope tube and the hand-piece; and
wherein the second portion is fixed to the other one of the proximal end and the hand-piece to which the first portion is not attached, such that as the proximal end rotates relative to the hand-piece, the first portion rotates relative to the second portion and detects the angle of rotation of the second portion, thereby detecting rotation of the proximal end of the endoscope tube relative to the hand-piece.

34. The endoscopic device of claim 1, wherein the endoscope tube is a rigid endoscope tube such that a rotation angle of the proximal end relative to the hand-piece indicates a rotation angle of the distal end relative to the hand-piece.

35. The endoscopic device of claim 1, wherein digital angle information indicating an angle of rotation between the proximal end of the endoscope tube relative to the hand piece is made available to the image processing pipeline where it is sampled periodically and quantized to a predetermined degree increment; and
wherein image rotation is performed by the image processing pipeline when a same quantized angle is observed consistently over a predetermined number of samples.

* * * * *